United States Patent [19]

Dziabo et al.

[11] Patent Number: 5,424,078

[45] Date of Patent: Jun. 13, 1995

[54] AQUEOUS OPHTHALMIC FORMULATIONS AND METHODS FOR PRESERVING SAME

[75] Inventors: Anthony J. Dziabo, El Toro; Paul S. Ripley, Irvine, both of Calif.

[73] Assignee: Allergan, Inc., Irvine, Calif.

[21] Appl. No.: 694,640

[22] Filed: May 2, 1991

Related U.S. Application Data

[63] Continuation-in-part of Ser. No. 277,791, Nov. 29, 1988.

[51] Int. Cl.$^6$ ............... A61K 33/14; A61K 31/19
[52] U.S. Cl. ..................... 424/661; 514/557; 514/912
[58] Field of Search ............... 424/661; 514/557, 912

[56] References Cited

U.S. PATENT DOCUMENTS

| Re. 32,672 | 5/1988 | Huth et al. | 252/95 |
|---|---|---|---|
| 2,436,134 | 2/1948 | Aston | 23/152 |
| 2,477,631 | 8/1949 | Levy | 8/105 |
| 3,123,521 | 3/1964 | Wentworth | 167/17 |
| 3,278,447 | 10/1966 | McNicholas | 167/17 |
| 3,591,515 | 7/1971 | Lovely | 252/187 |
| 3,819,828 | 6/1974 | McCoy | 424/71 |
| 3,910,296 | 10/1975 | Karageozian et al. | 134/2 |
| 4,084,747 | 3/1978 | Alliger | 424/65 |
| 4,104,190 | 8/1978 | Hartshorn | 252/187 R |
| 4,123,376 | 10/1978 | Gray | 252/99 |
| 4,456,510 | 6/1984 | Murakami | 204/101 |
| 4,459,217 | 7/1984 | Bogie | 252/174.14 |
| 4,499,077 | 2/1985 | Stockel et al. | 424/149 |
| 4,568,517 | 2/1986 | Kaspar et al. | 422/30 |
| 4,614,549 | 9/1986 | Ogunbuyi et al. | 134/19 |
| 4,618,444 | 10/1986 | Hudson et al. | 252/92 |
| 4,654,208 | 3/1987 | Stockel et al. | 424/78 |
| 4,689,215 | 8/1987 | Ratcliff | 424/53 |
| 4,690,773 | 9/1987 | Ogunbuyi et al. | 252/174.12 |
| 4,696,811 | 9/1987 | Ratcliff | 424/53 |
| 4,786,492 | 11/1988 | Ratcliff | 424/53 |
| 4,788,053 | 11/1988 | Ratcliff | 424/53 |
| 4,792,244 | 12/1988 | Ratcliff | 424/53 |
| 4,793,989 | 12/1988 | Ratcliff | 424/53 |
| 4,837,009 | 6/1989 | Ratcliff | 424/53 |
| 4,851,213 | 7/1989 | Ratcliff | 424/53 |
| 4,855,135 | 8/1989 | Ratcliff | 424/127 |

FOREIGN PATENT DOCUMENTS

| 0168253 | 1/1986 | European Pat. Off. . |
|---|---|---|
| 0196075 | 10/1986 | European Pat. Off. . |
| 0199385 | 10/1986 | European Pat. Off. . |
| 0279401 | 2/1988 | European Pat. Off. . |
| 1269677 | 4/1982 | United Kingdom . |
| 2139260 | 11/1984 | United Kingdom . |
| 2187748 | 9/1987 | United Kingdom . |
| WO8504107 | 9/1985 | WIPO . |
| WO8605695 | 10/1986 | WIPO . |

*Primary Examiner*—Zohreh Fay
*Attorney, Agent, or Firm*—Frank J. Uxa

[57] ABSTRACT

Stabilized chlorine dioxide is a preservative for ophthalmic formulations. The stabilized chlorine dioxide, when employed as a preservative ophthalmic formulations is preferably present in an amount of from about 0.0002 or about 0.002 to about 0.02 weight/volume percent. The aqueous ophthalmic formulations, in addition to the stabilized chlorine dioxide and the water which functions as a vehicle for the formulations, contains an ophthalmically acceptable tonicity component effective to maintain the osmolality of the formulation at least about 200 mOsmol/kg, and a buffer to maintain the pH of the ophthalmic formulation within an acceptable physiological range. A method for preserving aqueous ophthalmic formulations utilizing stabilized chlorine dioxide is also set forth.

18 Claims, No Drawings

5,424,078

AQUEOUS OPHTHALMIC FORMULATIONS AND METHODS FOR PRESERVING SAME

Related Application

This application is a continuation-in-part of application Ser. No. 277,791, filed Nov. 29, 1988. The disclosure of this prior application is hereby incorporated in its entirety herein by reference.

BACKGROUND OF THE INVENTION

The present invention relates to preserving ophthalmic formulations or compositions, such as solutions. More particularly it relates to the use of stabilized chlorine dioxide to preserve ophthalmic formulations.

The use of contact lens has become widespread as a replacement for conventional eye glasses because of the improved vision obtained by the wearer or for aesthetic reasons. Contact lenses accumulate microorganisms and cellular debris from the eye. Thus, the lenses must be periodically removed and cleaned to prevent irritation of the eye or infection. Formulations used in lens care must be preserved by some means to interdict introducing microbial contaminants onto contact lenses or into the eye. Disinfecting preparations are part of the regimen indicated for contact lens care.

Numerous ophthalmic formulations have heretofore been used with lenses. The composition of the ophthalmic formulation will often be dictated by the polymeric materials employed in the fabrication of the contact lens. Because of the chemical composition of most ophthalmic formulations, the contact lenses treated, e.g., disinfected, cleaned, soaked, and the like, in such formulations must be rinsed prior to placement in the wearer's eye to prevent irritation of the eye.

Problems have also been encountered in the use of the prior art ophthalmic formulations for the treatment of contact lenses in that such formulations often become contaminated or deteriorate when exposed to the atmosphere once the seal of he formulation container has been broken. Microorganisms and/or other impurities often contaminate the formulation which requires that the formulation be discarded. Thus, there exists a need for aqueous ophthalmic compositions having extended lives. In other words, there is a need for ophthalmic formulations which are effectively preserved without being irritating or otherwise damaging to the eye. It is to such preserved ophthalmic formulations and methods for preserving ophthalmic formulations that the present invention is directed.

Ratcliff U.S. Pat. Nos. 4,696,811 and 4,689,215 disclose the use of stabilized chlorine dioxide for the treatment and prevention of oral disease, for the reduction of malodor, as an anti-plaque agent, an anti-gingivitis and anti-peridontitis agent, as well as a denture soak. These two patents disclose the use of 0.005 percent to 0.02 percent stabilized chlorine dioxide in sterilized water as a contact lens soaking formulation. However, the patents are void of any teaching or suggestion that stabilized chlorine dioxide can be incorporated into an ophthalmic formulation as a preservative for such a formulation. In addition, the patents do not disclose the use of buffer or tonicity components.

Stockel et al U.S. Pat. No. 4,499,077 discloses an antimicrobial composition for soft contact lenses including an oxidizing agent such as an oxyhalogen compound, e.g., stabilized chlorine dioxide, or hydrogen peroxide, and a polymeric germicide, e.g., a quaternary ammonium polymer or an amino and/or imino polymer or salts thereof. Stockel et al U.S. Pat. No. 4,654,208 discloses an antimicrobial composition for contact lenses including an aqueous solution of a germicidal polymeric nitrogen compound and an oxidizing agent, e.g., chlorine dioxide, stabilized chlorine dioxide or hydrogen peroxide, to potentiate the activity of the germicidal polymeric nitrogen compound at low concentrations. The Stockel et al patents characterize the "polymeric germicides" and the "germicidal polymeric nitrogen compounds" as positively charged, nitrogen-containing cationic polymers, such as certain quaternary ammonium polymers and polymeric amino and/or imino compounds, e.g., polydiguanides. Neither of these Stockel et al patents relate to ophthalmic compositions without such positively charged, nitrogen-containing cationic polymers.

SUMMARY OF THE INVENTION

Broadly, the present invention relates to aqueous ophthalmic formulations containing an effective minor amount of stabilized chlorine dioxide to effectively preserve the ophthalmic formulation; a buffer component and a tonicity component. The present ophthalmic formulations are effectively preserved and can be used, e.g., in the contact lens care context, without causing irritation or discomfort to the eyes of the user of the formulations.

In one aspect, the present invention relates to aqueous ophthalmic formulations or compositions, for example, solutions, comprising water, e.g., as a vehicle; an amount, preferably from about 0.0002 or about 0.002 to about 0.02 weight/volume percent, of stabilized chlorine dioxide effective to act as the sole preservative in the formulation; at least one buffer component in an amount effective to maintain the pH of the formulation in the range of about 6.8 to about 8; and at least one tonicity component in an amount effective to maintain the formulation at an osmolality of at least about 200 mOsmol/kg, especially at a tonicity value substantially corresponding to the tonicity value of fluids of an eye. The present ophthalmic formulations preferably include substantially no, i.e., are substantially free of, germicidally effective amounts of any positively charged, nitrogen-containing cationic polymers, for example, the quaternary ammonium polymers, the polymeric amino and/or imino compounds and their salts disclosed in the above-noted Stockel et al patents. More preferably, the present ophthalmic formulations are substantially free of any such positively charged, nitrogen-containing cationic polymers. To provide the ophthalmic formulations with a pH substantially corresponding to the pH of the fluids of the eye, the pH of the ophthalmic formulation can be adjusted, if required, by addition of an acid or a base.

Methods for preserving ophthalmic formulations are also disclosed.

DETAILED DESCRIPTION

Stabilized chlorine dioxide has been found to be effective as a sole preservative in preserving ophthalmic formulations or compositions. Thus, the present formulations include stabilized chlorine dioxide in an amount effective to act as the sole preservative in the formulations. Although one or more other preservatives may be present, it is preferred that the formulations include no other effective preservatives. In a particularly useful embodiment, the present formulations preferably include no germicidally effective amount of any positively charged, nitrogen-containing cationic polymers, such as those disclosed in the above-noted Stockel et al patents. Still more preferably, the present formulations are substantially free of any quaternary ammonium compounds. Since stabilized chlorine dioxide has been found to be effective as the sole preservative for ophthalmic formulations, the presence of such nitrogen-containing cationic polymers and quaternary ammonium compounds, which can result in eye irritation or discomfort, is not needed.

The preserving amount of stabilized chlorine dioxide incorporated into an ophthalmic formulation (that is, to prevent microbial growth in the formulation) can vary widely but will generally be an amount sufficient to preserve the composition, for example, the physical and/or chemical integrity of the formulation. The presence of stabilized chlorine dioxide enhances, even greatly enhances, or prolongs the useful or shelf life of the present ophthalmic formulations.

The present formulations preserved with stabilized chlorine dioxide can be used in treating or caring for contact lenses made of a wide variety of different materials, such as different polymeric materials, without any substantial degradation of the lenses.

The thus treated or cared for contact lenses, such as lenses cleansed and soaked using an ophthalmic formulation in accordance with the present invention, can often be placed directly into the wearer's eye without the additional requirement of rinsing to remove residual formulation therefrom. Thus, contamination of the treated or cared for lenses can be substantially eliminated prior to placement in the wearer's eye.

Further, an effective disinfectant can be provided which effectively kills microorganisms which may be present on ophthalmic devices, for example, contact lenses. The disinfectant comprises at least 0.02 weight/volume percent stabilized chlorine dioxide as the disinfecting agent, for example, as the sole disinfecting agent.

The term "stabilized chlorine dioxide" is well known in the industry and by those skilled in the art. Stabilized chlorine dioxide includes one or more chlorine dioxide precursors such as one or more chlorine dioxide-containing complexes and/or one or more chlorite-containing components and/or one or more other entities capable of decomposing or being decomposed in a liquid, preferably aqueous, medium to form chlorine dioxide. U.S. Pat. No. No. 2,271,242 discloses a form of stabilized chlorine dioxide and a method for producing same which can be used as a preservative for aqueous ophthalmic solutions or as a disinfectant for ophthalmic devices. The disclosure of this patent is hereby incorporated in its entirety by reference herein. The manufacture or production of certain stabilized chlorine dioxide products is described in McNicholas U.S. Pat. No. 3,278,447, the disclosure of which is hereby incorporated in its entirety by reference herein. A commercially available stabilized chlorine dioxide which can be utilized in the practice of the present invention is the proprietary stabilized chlorine dioxide of BioCide International, Inc. of Norman, Okla., sold under the trademark Purogene. Other suitable stabilized chlorine dioxide products include that sold under the trademark Dura Klor by Rio Linda Chemical Company, Inc., and that sold under the trademark Antheium Dioxide by International Dioxide, Inc.

One aspect of the present invention resides in the use of a preserving amount of stabilized chlorine dioxide in aqueous ophthalmic formulations. It has been found that ophthalmic devices contacted with an aqueous ophthalmic formulation containing a preserving amount of stabilized chlorine dioxide and effective amounts of at least one of each of buffer and tonicity components often do not have to be rinsed to remove residual formulation prior to use, e.g., in the eye. Similarly, when such formulations are employed in a regimen of contact lens care, the contact lenses can often be placed in a wearer's eye, without rinsing, without irritation or adverse effects occurring to the tissue of the eye, and without discomfort.

The amount of stabilized chlorine dioxide incorporated in the ophthalmic formulation as a preservative can vary widely provided that such amount effectively prevents microbial growth in the formulation. The amount of stabilized chlorine dioxide included in the formulation is preferably in the range of about 0.0002 or about 0.002 to about 0.02, more preferably about 0.004 to about 0.01, weight/volume percent of the formulation.

In order to provide that the aqueous ophthalmic formulation containing a preserving amount of stabilized chlorine dioxide does not irritate one's eye, it is important that the ophthalmic formulation have a pH value in the range of about 6.8 to about 8, preferably about 7 to about 7.5, and still more preferably so that the pH of the ophthalmic formulation substantially corresponds to the pH value of the fluids in the eye, in particular, the human eye.

To stabilize or maintain the ophthalmic formulation at the desired pH, an effective minor amount of at least one buffer component is incorporated into the ophthalmic formulation. The effective minor amount of buffer component employed to buffer or maintain the formulation at the desired pH can vary widely and depends to a large degree on the particular buffer component employed, as well as the chemical composition of the ophthalmic formulation. However, desirable results have been obtained when the amount of buffering component incorporated into the aqueous ophthalmic formulation to stabilize the formulation at an acceptable physiological pH is in the range of about 0.05 to about 1 weight/volume percent of the formulation.

Any suitable buffer component can be employed which is compatible with the other ingredients of the ophthalmic formulation, and which does not have deleterious or toxic properties which could harm the eye. Examples of suitable ophthalmically acceptable buffer components include acetate buffers, citrate buffers, phosphate buffers, borate buffers and mixtures thereof. Specific buffer components useful in the present invention include boric acid, sodium borate, sodium phosphates, including mono, di- and tri-basic phosphates, such as sodium phosphate monobasic monohydrate and sodium phosphate dibasic heptahydrate, and mixtures thereof. It should be noted that any other suitable ophthalmically acceptable buffer components can be employed to maintain the pH of the ophthalmic formulation so that the ophthalmic formulation is provided with an acceptable pH, and the before-mentioned buffer components are merely examples of such buffer components.

When it is determined that the buffered ophthalmic formulation does not have the desired pH value, the pH of the aqueous buffered ophthalmic formulation can be adjusted by the addition of an effective amount of either a base or an acid, as the case may be. Any suitable base or acid can be employed to adjust the pH of the aqueous buffered ophthalmic formulation which does not provide the ophthalmic formulation with toxic or deleterious properties which could harm either ophthalmic devices or the eye. An example of a base which can be used to adjust the pH of the aqueous buffered ophthalmic formulation is 1N sodium hydroxide; and an example of an acid which can be used to adjust the pH of the aqueous buffered ophthalmic formulation is 1N hydrochloric acid.

Further, in order to provide that the present ophthalmic formulations do not irritate the eye, e.g., the eye of the wearer of the contact lens treated using such formulations, it is important that the ophthalmic formulations have an osmolality (a measure of tonicity) of at least about 200 mOsmol/kg, preferably in the range of about 200 to about 350 or about 400 mOsmol/kg. In an especially useful embodiment, the osmolality or tonicity of the formulation substantially corresponds to the tonicity of the fluids of the eye, in particular the human eye.

Any suitable ophthalmically acceptable tonicity component or components may be employed, provided that such component or components are compatible with the other ingredients of the ophthalmic formulation and do not have deleterious or toxic properties which could harm the eye. Examples of useful tonicity components include sodium chloride, potassium chloride, mannitol, dextrose, glycerin, propylene glycol and mixtures thereof. In one embodiment, the tonicity component is selected from inorganic salts and mixtures thereof.

The amount of ophthalmically acceptable tonicity component utilized can vary widely. In one embodiment, the tonicity component is preferably present in the ophthalmic formulation in an amount in the range of about 0.5 to about 0.9 weight/volume percent of the formulation.

Typical of ophthalmically acceptable inorganic salt tonicity components are alkali metal chlorides and alkaline earth metal chlorides, such as sodium chloride, potassium chloride, calcium chloride and magnesium chloride.

The formulations of the present invention include an ophthalmically acceptable medium, preferably an ophthalmically acceptable liquid aqueous medium. This medium often acts as a vehicle or carrier, e.g., as a solvent, for the other components in the formulation. A material is "ophthalmically acceptable" if the material can be placed into a mammalian eye without causing any substantial damage or harm to the eye. One particularly useful ophthalmically acceptable medium is water. Preferably, the medium, and in fact the entire formulation, is sterile.

As previously set forth, the stabilized chlorine dioxide can also be utilized as a disinfecting agent in a disinfectant composition. When formulating such a disinfectant composition a suitable vehicle, such as sterilized water, is employed and at least about 0.02 weight/volume percent stabilized chlorine dioxide is incorporated as the disinfecting agent. While the amount of stabilized chlorine dioxide employed as the disinfecting agent can vary widely, desirable results can be obtained when the stabilized chlorine dioxide utilized as the disinfecting agent is present in the disinfectant composition in an amount of from about 0.02 to 2.0 weight/volume percent, desirably from about 0.04 to about 0.1 weight/volume percent, and more desirably from about 0.05 to about 0.08 weight/volume percent.

One or more additional components can be included in the present formulations based on the particular application for which the formulations are made. Thus, the present formulations can be made up as disinfecting compositions, cleaning compositions, wetting compositions, conditioning compositions, soaking compositions and the like. Also, the present formulations can be made up to be useful in performing two or more contact lens caring operations. For example, a disinfecting/cleaning formulation, or a cleaning/conditioning composition or even an all purpose lens care formulation can be made up and such multi-functional formulations are included within the scope of the present invention.

The additional component or components included in the present formulation are chosen to impart or provide at least one beneficial or desired property to the formulations. Such additional components may be selected from components which are conventionally used in one or more contact lens care compositions. Examples of such additional components include cleaning agents, wetting agents, nutrient agents, sequestering agents, viscosity builders, contact lens conditioning agents, antioxidants, and the like. These additional components are each included in the present formulations in an amount effective to impart or provide the beneficial or desired property to the compositions. For example, such additional components may be included in the present formulations in amounts similar to the amounts of such components used in other, e.g., conventional, contact lens care products.

Examples of useful wetting agents include polyvinyl alcohol, polyoxamers, polyvinyl pyrrollidone, hydroxypropyl methyl cellulose and mixtures thereof.

Examples of useful sequestering agents include disodium ethylene diamine tetraacetate, alkali metal hexametaphosphate, citric acid, sodium citrate and mixtures thereof.

Examples of useful viscosity builders include hydroxyethyl cellulose, hydroxymethyl cellulose, polyvinyl pyrrolidone, polyvinyl alcohol and mixtures thereof.

Examples of useful antioxidants include sodium metabisulfite, sodium thiosulfate, N-acetylcysteine, butylated hydroxyanisole, butylated hydroxytoluene and mixtures thereof.

The present formulations may be used in the care of a contact lens, e.g., to disinfect the lens, to preserve the lens, to otherwise treat the lens and/or to make wearing the lens more safe and comfortable. The present formulations, made up appropriately by blending or combining the various components of the formulation together, may be used in conventional contact lens care regimens by using the present formulations, in place of prior conventional compositions. In many instances, these contact lens care regimens involve contacting the lens with the present formulation in an amount, and at conditions, effective to obtain the beneficial or desired contact lens care result.

For example, a contact lens to be disinfected may be contacted with a disinfecting composition, e.g., aqueous solution, according to the present invention, preferably at a temperature in the range of about 0° C. to about 100° C., more preferably in the range of about 10° C. to about 60° C. and still more preferably in the range of about 15° C. to about 30° C. Contacting at or about ambient temperature is very convenient and useful. The contacting preferably occurs at or about atmospheric pressure. The contacting preferably occurs for a time to substantially disinfect the lens being treated. Such contacting times can be in the range of about 1 minute to about 12 hours or more.

After this contacting, the disinfected contact lens can be taken from the composition and placed directly in an eye, e.g., a human eye, for safe and comfortable wear. Alternately, after being disinfected, the contact lens can be contacted with a second medium, e.g., a liquid aqueous medium such as a preserved isotonic saline solution in accordance with the present invention, prior to being placed in the eye of the wearer of the disinfected contact lens.

The contact lens care formulations disclosed herein are adaptable for use in most types of contact lens care equipment, such as ultrasonic cleaners and the like.

In order to more fully describe the present invention the following examples are set forth. However, the examples are merely illustrative in purpose and are not intended to be limiting upon the inventive concept as set forth in the appended claims.

EXAMPLE I

A series of experiments were performed to determine the antimicrobial properties of a borate buffered saline solution preserved with stabilized chlorine dioxide. The stabilized chlorine dioxide employed was the proprietary stabilized chlorine dioxide of Bio-Cide International, Inc. of Norman, Oklahoma, sold under the trademark Purogene. The concentration of the stabilized chlorine dioxide added to the borate buffered saline solution was varied.

The borate buffered saline solution had the following composition.

| Ingredients | Percent (Weight/Volume) |
| --- | --- |
| Sodium Chloride USP | 0.85 |
| Boric Acid NF | 0.10 |
| Purified water USP* | To 100 ml |

*Quantity sufficient (Q.S.) to provide 100 ml of solution.

The pH of the buffered solution was adjusted by the addition of either hydrochloric acid NF or sodium hydroxide NF so that the pH of the saline solution was within the range of about 7.7 to 7.9.

The stabilized chlorine dioxide was added to the borate buffered saline solution in the following concentrations:

| Percent (weight/volume) |
| --- |
| 0.005 |
| 0.004 |
| 0.003 |
| 0.002 |

Each of the above concentrations of stabilized chlorine dioxide exhibited the desired preservative properties for the borate buffered saline solution. Further, all four concentrations of the stabilized chlorine dioxide exhibited good antimicrobial activity, with the three highest concentrations achieving total bacterial kill after 24 hours. Tests indicated that total kill of bacteria was achieved by the solution containing 0.002 weight/volume percent stabilized chlorine dioxide after seven days.

EXAMPLE II

To compare the preservative efficacy of stabilized chlorine dioxide on a borate buffered ophthalmic solution, a preserving amount of stabilized chlorine dioxide having a raw material age of 54 months was utilized in one sample; and a similar preserving amount of stabilized chlorine dioxide having a raw material age of about 2 months was utilized in a second sample. Each of the samples of stabilized chlorine dioxide was the proprietary stabilized chlorine dioxide of Bio-Cide International, Inc. of Norman, Okla., sold under the trademark Purogene. No aging effect was detected between the two samples and their use as a preservative for borate buffered saline solutions. However, the aged stabilized chlorine dioxide (54 month age) possessed a slightly superior activity against the yeast *C. albicans*.

EXAMPLE III

A preservative efficacy test was performed on a borate buffered saline solution having a composition similar to that of Example I wherein 0.005 weight/volume percent stabilized chlorine dioxide was added to the borate buffered solution and the resulting mixture stored for 90 days at 45° C. At the end of the storage period, the sample was examined and it was determined that the stabilized chlorine dioxide was an effective preservative for a borate buffered saline solution.

EXAMPLE IV

An experiment was conducted to determine if a borate buffered saline solution containing 0.005 weight/volume percent stabilized chlorine dioxide met the USP Efficacy criteria for ophthalmics as set forth in the U.S. Pharmacopeia (USP XXI, 1985). The stabilized chlorine dioxide employed was the proprietary stabilized chlorine dioxide of Bio-Cide International, Inc. of Norman, Okla., sold under the trademark Purogene. The criteria for preservatives requires that a 99.9% reduction of microbes challenge occur within 14 days of contact with the product being tested; and that no growth of yeast and fungi occur.

The borate buffered saline solution containing 0.005 weight/volume percent stabilized chlorine dioxide met the before-mentioned criteria for preservatives. However, a control solution of the borate buffered saline solution which did not contain the stabilized chlorine dioxide present did not meet this USP Efficacy criteria for ophthalmics.

EXAMPLE V

A 21 day subacute eye toxicity study in rabbits was conducted using a borate buffered saline solution containing 0.005 weight/volume percent stabilized chlorine dioxide. The stabilized chlorine dioxide was as identified in Example I. The borate buffered saline solution containing the stabilized chlorine dioxide had the following composition:

| Ingredients | Percent (weight/volume) |
| --- | --- |
| Stabilized Chlorine Dioxide | 0.005 |
| Sodium Chloride USP | 0.85 |
| Boric Acid NF | 0.10 |
| Purified Water USP* | To 100 ml |

*Quantity sufficient (Q.S.) to provide 100 ml solution.

The pH of the above buffered saline solution was adjusted so that the pH of the solution was between 7.7 and 7.9.

The ocular effects of the buffered saline solution containing 0.005 weight/volume percent stabilized chlorine dioxide were evaluated in rabbit eyes in conjunction with Permalens soft contact lenses. Test eye lenses were subjected to daily cleaning, rinsing, and overnight soaking with the borate buffered saline solution containing stabilized chlorine dioxide. Control eye lenses were subjected to the same regimen using preserved normal saline solution. Lenses were fit directly to the eye and worn daily for a minimum of 8 hours for 21 consecutive days.

Eyes were observed daily for discomfort at lens insertion and for gross ocular reactions at lens removal. Slit lamp biomicroscopy was performed weekly. Pachometry and rose bengal staining were performed at the conclusion of the experiment. Histopathological evaluation was performed on eyes from three animals. No significant ocular reactions were noted.

The following is a summation of the results of the experiments set forth above:
A. Discomfort: No ocular discomfort was noted at lens insertion throughout the study.
B. Gross Observations: At the time of lens removal, +1 hyperemia was noted in one control eye on Day 17. No other ocular reactions were noted.
C. Slit Lamp Examinations (Days 7, 14 and 21): No ocular reactions were noted in any rabbit.
D. Corneal Metabolism (Days 7, 14 and 21).: No test related changes in corneal metabolism, as measured by corneal thickness, were noted throughout the study.
E. Cytotoxicity (Day 21): Rose bengal staining appeared normal in both eyes of all rabbits, indicating that corneal epithelial cell vitality was not affected by the solution tested.
F. Histopathological Evaluation: No microscopic changes which can be specifically related to the test regimen were apparent among the eyes and extraocular tissues examined. There were no predictable microscopic differences observed when comparing the test eyes and extraocular tissues with the control eyes and extraocular tissues.

The above data indicates that a borate buffered saline solution containing 0.005 weight/volume percent stabilized chlorine dioxide, in conjunction with Permalens soft contact lenses, is not discomforting, irritating, toxic or cytotoxic to rabbit eyes following 21 consecutive days of testing.

EXAMPLE VI

A 1 day acute eye toxicity and cytotoxicity study in rabbits was conducted using a borate buffered saline solution containing 0.005 weight/volume percent stabilized chlorine dioxide. The stabilized chlorine dioxide was as identified in Example I. The borate buffered saline solution containing the stabilized chlorine dioxide had the following composition:

| Ingredients | Percent (weight/volume) |
|---|---|
| Stabilized Chlorine Dioxide | 0.005 |
| Sodium Chloride USP | 0.85 |
| Boric Acid NF | 0.10 |
| Purified Water USP* | To 100 ml |

*Quantity Sufficient (Q.S.) to provide 100 ml solution.

The pH of the above buffered saline solution was adjusted so that the pH of the solution was between 7.7 and 7.9.

The ocular effects of the buffered saline solution containing 0.005 weight/volume percent stabilized chlorine dioxide were evaluated in rabbit eyes in conjunction with Permalens soft contact lenses and multiple topical instillations. Test eye lenses were subjected to overnight soaking in the borate buffered saline solution containing 0.005 weight/volume percent stabilized chlorine dioxide followed by direct fit to the eye and 8 hours of wear with topical instillations of the test solution performed at a rate of one drop every one-half hour. Eyes were observed for discomfort and/or gross ocular reactions at lens fit, at each instillation and at lens removal. Slip lamp biomicroscopy was performed following lens removal. Control eyes were subjected to the same regimen using preserved normal saline.

The following is a summation of the results of the experiments set forth above:
A. Discomfort: No ocular discomfort was noted at lens fit or at any instillation period throughout the study.
B. Gross Observations: No ocular reactions were noted at any instillation period or at lens removal.
C. Slip Lamp Examinations: No ocular reactions were noted in any rabbit.
D. Cytotoxicity Rose bengal staining appeared normal in both eyes of all rabbits, indicating that epithelia cell vitality was not affected by the solutions tested.

The above data indicates that a borate buffered saline solution containing 0.005 weight/volume percent stabilized chlorine dioxide, in conjunction with Permalens soft contact lenses, is not discomforting, irritating, toxic or cytotoxic to rabbit eyes following this exaggerated method of testing.

EXAMPLE VII

An acute eye toxicity and cytotoxicity study in rabbits was conducted using a borate buffered saline solution containing 0.005 weight/volume percent stabilized chlorine dioxide. The stabilized chlorine dioxide was that identified in Example I. The borate buffered saline solution containing the stabilized chlorine dioxide had the following composition:

| Ingredients | Percent (weight/volume) |
|---|---|
| Stabilized Chlorine Dioxide | 0.005 |
| Sodium Chloride USP | 0.85 |
| Boric Acid NF | 0.10 |
| Purified water USP* | To 100 ml |

*Quantity Sufficient (Q.S.) to provide 100 ml solution.

The pH of the above buffered saline solution was adjusted so that the pH of the solution was between 7.7 and 7.9.

The ocular effects of the buffered saline solution containing 0.005 weight/volume percent stabilized chlorine dioxide were evaluated in rabbit eyes following 1 day of multiple topical instillations performed at a rate of one drop every one-half hour for 8 hours. Test eyes were treated with the borate buffered saline solution containing 0.005 weight/volume percent stabilized chlorine dioxide and control eyes were treated with a preserved normal saline solution.

Eyes were observed for discomfort and/or gross ocular reactions at each instillation. Slit lamp biomicroscopy was performed following the last instillation period. No ocular reactions were noted in the test eyes.

The following is a summation of the results of the experiments set forth above:
A. Discomfort: +1 discomfort, lasting up to 30 seconds, was noted in the control eye at 3 of 48 instillations involving two of three rabbits.
B. Gross Observations: No ocular reactions were noted at any instillation period.
C. Slit Lamp Examinations: No ocular reactions were noted in any rabbit.
D. Cytotoxicity: Rose bengal staining appeared normal in both eyes of all rabbits, indicating that epithelial cell vitality was not affected by the preparations tested.

The above data indicates that a borate buffered saline solution containing 0.005 weight/volume percent stabilized chlorine dioxide is not discomforting, irritating, toxic or cytotoxic to rabbit eyes following this exaggerated method of testing.

EXAMPLE VIII (COMPARATIVE)

A series of compositions were prepared using sterilized distilled water and varying concentrations of the proprietary stabilized chlorine dioxide sold by Bio-Cide International, Inc. of Norman, Okla., under the trademark Purogene.

Each of these compositions was tested to determine its pH and osmolality. After the compositions were prepared, they were allowed to equilibrate overnight before the pH and osmolality were determined.

Results of these tests were as follows:

| Concentration of Stabilized Chlorine Dioxide, (w/v) % | pH | Osmolality, mOsmol/kg |
| --- | --- | --- |
| 0.005 | 6.4 | 5 |
| 0.02 | 6.8 | 13 |
| 0.1 | 8.6 | 55 |
| 0.2 | 9.0 | 105 |

These results indicate that simple solutions of stabilized chlorine dioxide in sterilized water have varying pHs, which are often outside the range of about 6.8 to about of the present compositions. Also, such simple solutions have tonicity values or osmolalities substantially outside the range of at least about 200 mOsmol/kg of the present compositions. Put another way, such simple aqueous stabilized chlorine solutions are not effective to provide preserved compositions which are ophthalmically acceptable or compatible with the eye so as to be used without eye discomfort or irritation.

While this invention has been described with respect to various specific examples and embodiments, it is to be understood that the invention is not limited thereto and that it can be variously practiced within the scope of the following claims.

What is claimed is:

1. A method for preserving an aqueous ophthalmic formulation so as to enhance the shelf life thereof comprising incorporating into said aqueous ophthalmic formulation stabilized chlorine dioxide in an amount effective to act as the sole preservative in said aqueous ophthalmic formulation, at least one ophthalmically acceptable buffer component in an amount effective to maintain said aqueous ophthalmic formulation at a pH in the range of about 6.8 to about 8, and at least one ophthalmically acceptable tonicity component in an amount effective to maintain said aqueous ophthalmic formulation at an osmolality of at least about 200 mOsmol/kg, provided that said aqueous ophthalmic formulation is ophthalmically acceptable and no germicidally effective amounts of any positively charged, nitrogen-containing cationic polymers are incorporated into said aqueous ophthalmic formulation.

2. The method of claim 1 wherein said stabilized chlorine dioxide is present in said aqueous ophthalmic formulation in an amount in the range of about 0.0002 to about 0.02 weight/volume percent.

3. The method of claim 1 wherein said stabilized chlorine dioxide is present in said aqueous ophthalmic formulation in an amount in the range of about 0.004 to about 0.01 weight/volume percent.

4. The method of claim 1 wherein said at least one ophthalmically acceptable buffer component is present in an amount effective to maintain said aqueous ophthalmic formulation at a pH in the range of about 7 to about 7.5.

5. The method of claim 1 wherein said at least one ophthalmically acceptable tonicity component is present in an amount effective to maintain said aqueous ophthalmic formulation at an osmolality in the range of about 200 to about 400 mOsmol/kg.

6. The method of claim 1 wherein said aqueous ophthalmic formulation is a solution.

7. A method for preserving an aqueous ophthalmic solution so as to enhance the shelf life thereof comprising incorporating into said aqueous ophthalmic solution stabilized chlorine dioxide in an amount effective to act as the sole preservative in said aqueous ophthalmic solution in the range of about 0.002 to about 0.02 weight/volume percent, at least one ophthalmically acceptable buffer component in an amount effective to maintain said aqueous ophthalmic solution at a pH in the range of about 6.8 to about 8, and at least one ophthalmically acceptable tonicity component in an amount effective to maintain said aqueous ophthalmic solution at an osmolality in the range of about 200 to about 400 mOsmol/kg, provided that said aqueous ophthalmic solution is ophthalmically acceptable and substantially no germicidally effective amounts of any positively charged, nitrogen-containing cationic polymers are incorporated into said aqueous ophthalmic solution.

8. A preserved ophthalmic formulation comprising an ophthalmically acceptable aqueous medium and, included therein, stabilized chlorine dioxide in an amount effective to act as the sole preservative in said ophthalmically acceptable aqueous medium, at least one ophthalmically acceptable buffer component in an amount effective to maintain said ophthalmically acceptable aqueous medium at a pH in the range of about 6.8 to about 8, and at least one ophthalmically acceptable tonicity component in an amount effective to maintain said ophthalmically acceptable aqueous medium at an osmolality of at least about 200 mOsmol/kg, provided that said preserved ophthalmic formulation is ophthalmically acceptable and is free of germicidally effective amounts of any positively charged, nitrogen-containing cationic polymers.

9. The preserved ophthalmic formulation of claim 8 wherein said stabilized chlorine dioxide is present in said preserved ophthalmic formulation in an amount in the range of about 0.0002 to about 0.02 weight/volume percent.

10. The preserved ophthalmic formulation of claim 8 wherein said stabilized chlorine dioxide is present in said preserved ophthalmic formulation in an amount in the range of about 0.004 to about 0.01 weight/volume percent.

11. The preserved ophthalmic formulation of claim 8 wherein said at least one ophthalmically acceptable tonicity component is selected from the group consisting of alkali metal chlorides and alkaline earth metal chlorides and mixtures thereof.

12. The preserved ophthalmic formulation of claim 8 wherein said at least one ophthalmically acceptable tonicity component comprises sodium chloride.

13. The preserved ophthalmic formulation of claim 8 wherein said at least one ophthalmically acceptable tonicity component comprises an alkaline earth metal salt selected from the group consisting of calcium chloride and magnesium chloride and mixtures thereof.

14. The preserved ophthalmic formulation of claim 8 wherein said at least one buffer component is selected from the group consisting of potassium phosphates, boric acid, sodium borate, sodium phosphates and mixtures thereof.

15. The preserved ophthalmic formulation of claim 8 wherein said at least one ophthalmically acceptable buffer component is present in an amount effective to maintain said ophthalmically acceptable aqueous medium at a pH in the range of about 7 to about 7.5.

16. The preserved ophthalmic formulation of claim 8 wherein said at least one ophthalmically acceptable tonicity component is present in an amount effective to maintain said ophthalmically acceptable aqueous medium at an osmolality in the range of about 200 to about 400 mOsmol/kg.

17. The preserved ophthalmic formulation of claim 8 which is a solution.

18. A preserved ophthalmic solution comprising an ophthalmically acceptable aqueous solution and, included therein, stabilized chlorine dioxide in an amount effective to act as the sole preservative in said ophthalmically aqueous acceptable solution in the range of about 0.002 to about 0.02 weight/volume percent, at least one ophthalmically acceptable buffer component in an amount effective to maintain said ophthalmically acceptable aqueous solution at a pH in the range of about 6.8 to about 8, and at least one ophthalmically acceptable tonicity component in an amount effective to maintain said ophthalmically acceptable aqueous solution at an osmolality in the range of about 200 to about 400 mOsmol/kg, provided that said preserved ophthalmic solution is ophthalmically acceptable and is free of germicidally effective amounts of any positively charged, nitrogen-containing polymers.

* * * * *